United States Patent [19]

Alexander et al.

[11] 4,209,013
[45] Jun. 24, 1980

[54] STERILE CONNECTION SYSTEM USING FLEXIBLE CONTAINER

[75] Inventors: John B. Alexander, Evanston; T. Michael Dennehey, Arlington Heights; Richard P. Goldhaber, Libertyville, all of Ill.

[73] Assignee: Baxter Travenol Laboratories, Inc., Deerfield, Ill.

[21] Appl. No.: 27,420

[22] Filed: Apr. 5, 1979

[51] Int. Cl.² .................................. A61J 7/00
[52] U.S. Cl. .................... 128/213 A; 128/247
[58] Field of Search .......... 128/213 A, 213 R, 214 R, 128/214 C, 214 G, 214.2, 247, 224, 227, 348

[56] References Cited

U.S. PATENT DOCUMENTS

| | | | |
|---|---|---|---|
| 3,064,653 | 11/1962 | Coanda | 128/348 |
| 3,951,145 | 4/1976 | Smith | 128/214 R |
| 3,993,066 | 11/1976 | Virag | 128/214 C |
| 4,048,995 | 9/1977 | Mittleman | 128/214 R |

FOREIGN PATENT DOCUMENTS 737249  6/1966  Canada ................. 128/214 G

Primary Examiner—John D. Yasko
Attorney, Agent, or Firm—Paul C. Flattery; George H. Gerstman

[57] ABSTRACT

A sterile connector system is provided for continuous ambulatory peritoneal dialysis in which a dialysate solution container having a transfer port is coupled to tubing extending from a patient's peritoneal cavity. The transfer port is connected to one end of a flexible housing and the patient's tubing is connected to the opposite end of the flexible housing. A sterilizing agent is introduced into the housing and in contact with the transfer port and the patient's tubing. The sterilized transfer port is thereafter connected to the sterilized patient's tubing within the housing.

28 Claims, 22 Drawing Figures

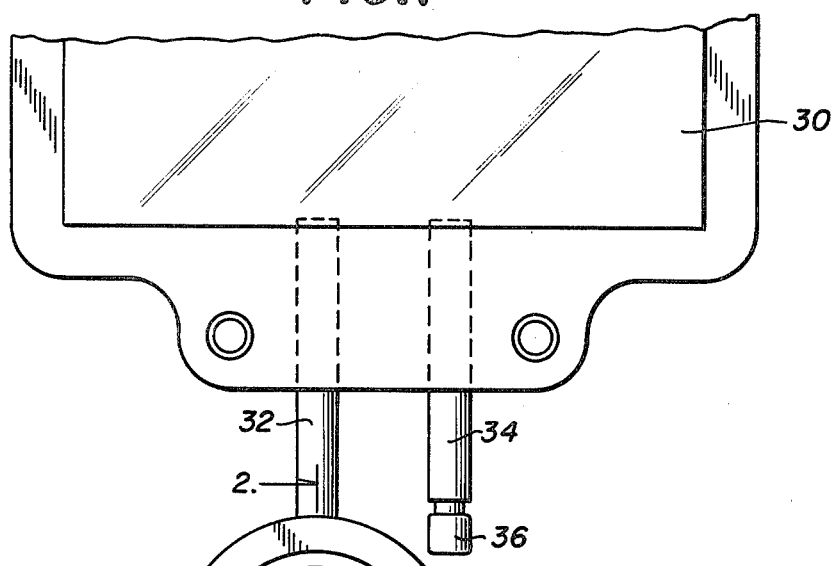
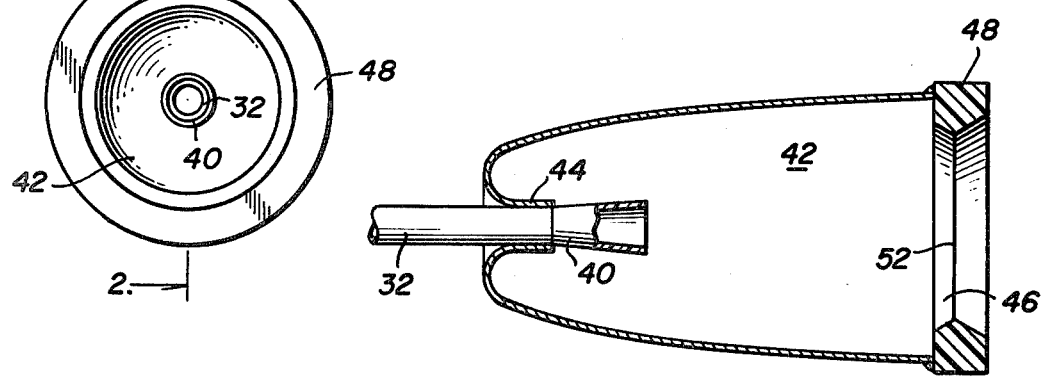
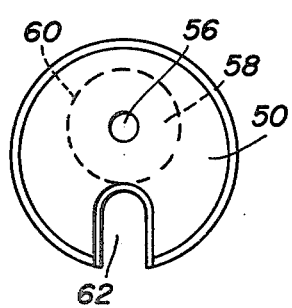
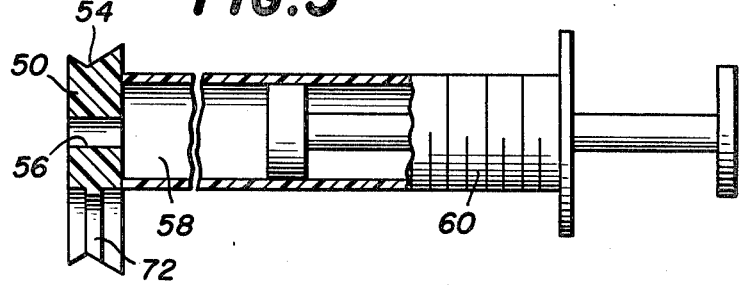
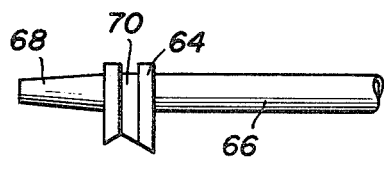
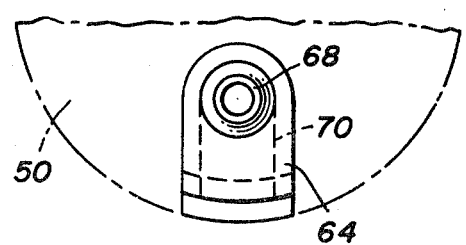

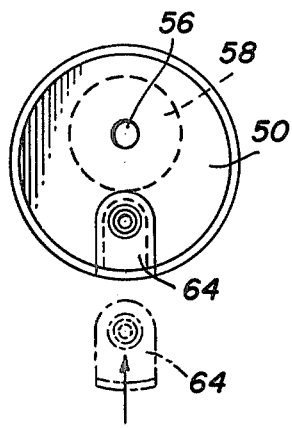
FIG. 7
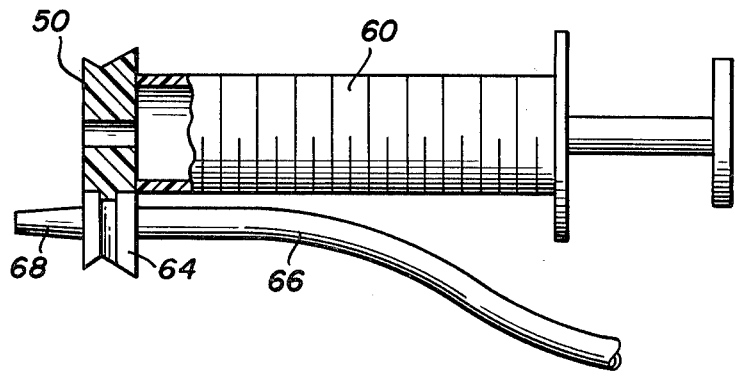
FIG. 8
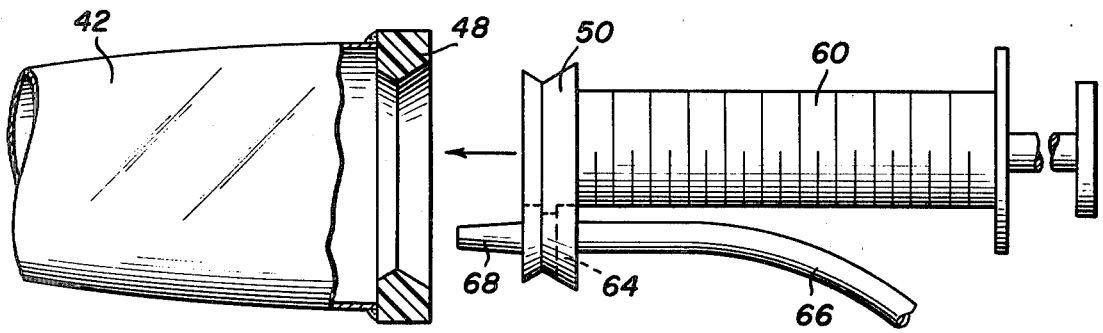
FIG. 9
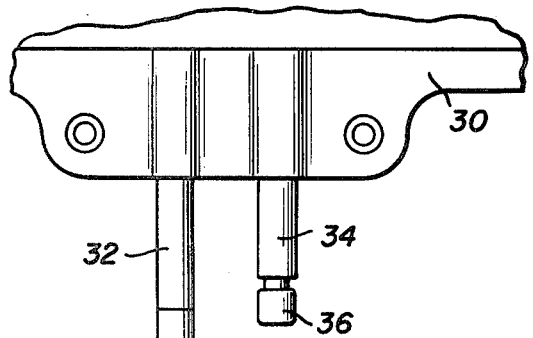
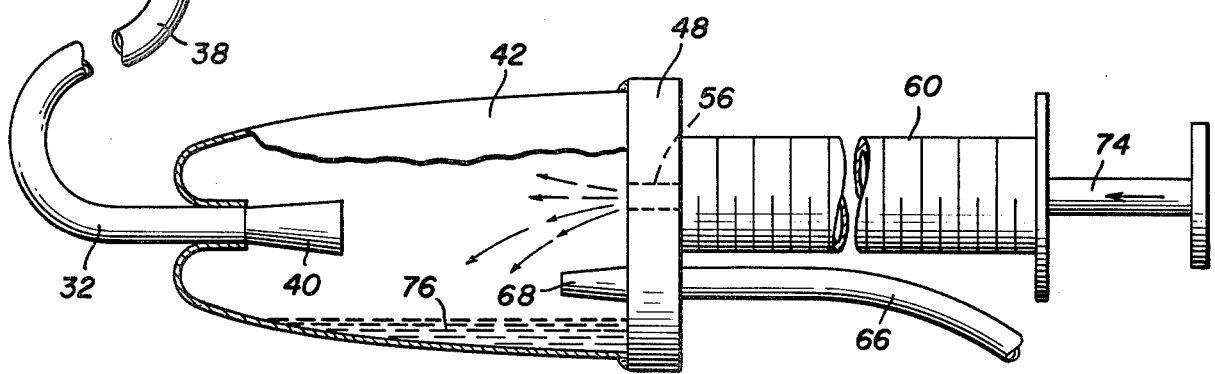
FIG. 10

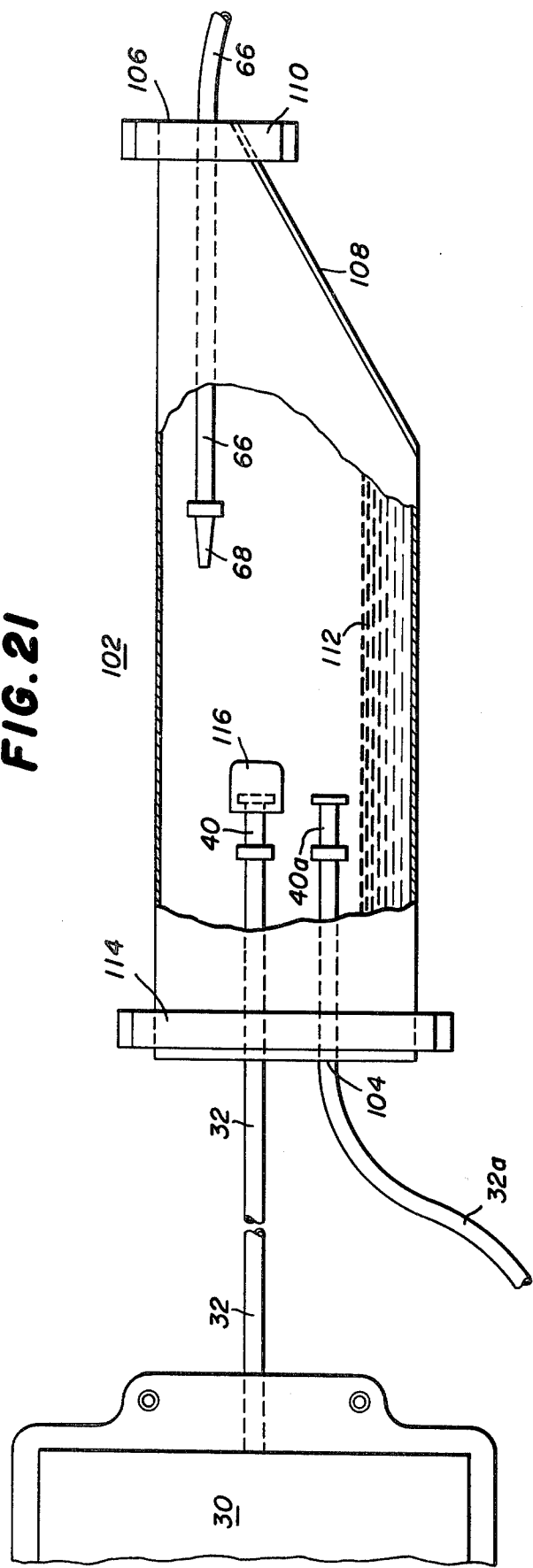
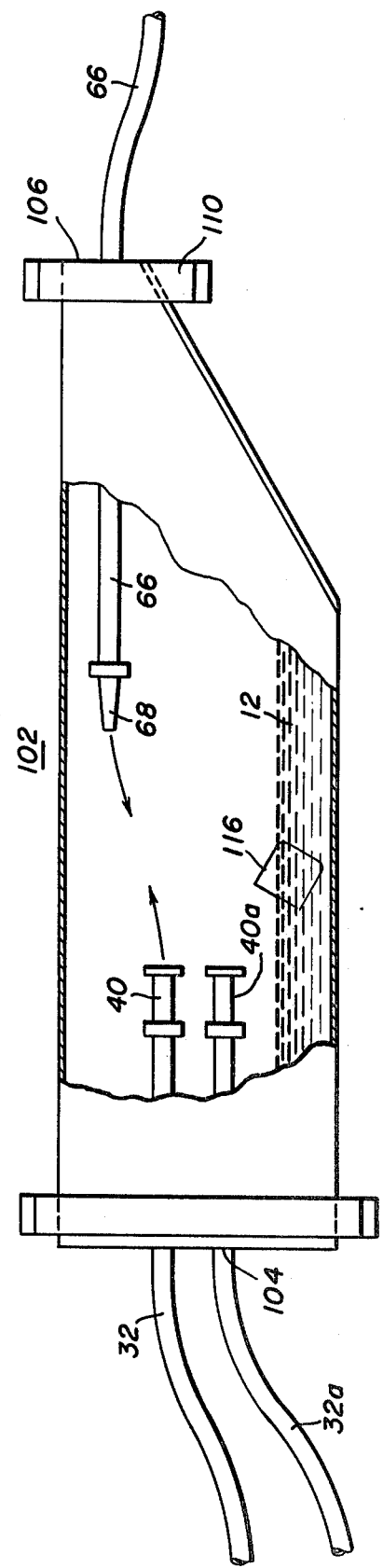

STERILE CONNECTION SYSTEM USING FLEXIBLE CONTAINER

BACKGROUND OF THE INVENTION

This invention concerns a novel sterile connection system for enabling the sterile connection of a first tube to a second tube. Although the illustrative embodiment of the invention is described in connection with tube transfer during ambulatory peritoneal dialysis, it is to be understood that other sterile tube transfers can be achieved in accordance with the present invention, such as the transfer of a tube from one blood bag to another. Thus, as used herein, the term "medical solution container" is intended to encompass containers of all shapes and materials and including any type of solution which may be introduced to a patient for medical purposes.

In many medical applications, it is necessary to remove a connector tube from a first medical solution container and to then introduce it to a second medical solution container. It is, of course, desirable and, on occasion, required that the transfer of the tube from one medical solution container to the other medical solution container be achieved in a sterile manner.

For example, in one type of ambulatory peritoneal dialysis, a tube which is coupled to the patient's peritoneal cavity is first connected to the transfer port (i.e., transfer tube) of a fresh dialysis solution container. For ambulatory purposes, the container is preferably in the form of a flexible plastic bag.

The dialysis solution is then introduced into the patient's peritoneal cavity via the transfer tube and the patient's tube and the dialysis solution is allowed to remain in the patient's peritoneal cavity for several hours, for example three to four hours. During this period of time, the patient's tube is not disconnected from the transfer tube, but the patient's tube may be clamped and the dialysis solution bag may be folded and carried by the patient.

Thereafter, the patient's tube is unclamped and the dialysis solution is drained back into the solution bag. Once the dialysis solution has been drained into the solution bag, the patient's tube is disconnected from the transfer tube of the used solution container and is inserted into the transfer tube of a fresh solution container. Thereupon the procedure is repeated. It is desirable, however, that during the disconnection of the patient's tube from the used dialysis solution container and connection of the patient's tube to a fresh dialysis solution container, that such connection be accomplished in a sterile manner. In addition, other medical procedures utilize similar connections which may desirably be accomplished in a sterile manner.

For example, in blood administration a tube coupled to a patient's vein is first inserted into the transfer port of a fresh blood bag. After the blood has been introduced from the fresh blood bag to the patient, it may be necessary to introduce blood from another blood bag to the patient. Under such conditions, the patient's tube is removed from the transfer port of the first blood bag and is inserted into the transfer port of another blood bag. The desirability of accomplishing such transfer in a sterile manner is apparent.

It is, therefore, an object of the present invention to provide a system for enabling the sterile transfer of a first tube from the transfer tube of a first medical container and to the transfer tube of another medical container.

Another object of the present invention is to provide sterile connection apparatus that is simple in construction and easy to manufacture.

A further object of the present invention is to provide a method for enabling a patient to connect, in a sterile manner, (a) a tube coupled to the patient to (b) a transfer tube of a medical solution container.

Other objects and advantages of the present invention will become apparent as the description proceeds.

SUMMARY OF THE INVENTION

In accordance with the invention, a sterile connection system is provided for continuous ambulatory peritoneal dialysis in which a dialysis solution container having a transfer port is coupled to tubing extending from a patient's peritoneal cavity. The improvement comprises a flexible housing having a first area thereof for attachment to the transfer port and a second, spaced area for attachment to the patient's tubing. The attachment areas define openings for enabling the transfer port and patient's tubing to extend within the interior of the flexible housing when they are attached thereto. The flexible housing has means for receiving a sterilizing fluid therein and is operable to enable the transfer port and the patient's tubing to be sterilized within the housing and also connected to each other within the housing.

In one embodiment of the invention, the flexible housing comprises a flexible pouch and means are provided for fastening the transfer port to the first attachment area. An adapter member is provided for connection to the second area to couple the patient's tubing to the flexible pouch. The adapter member has means for receiving a complimentary member carrying the patient's tubing and also has means for receiving a sterilizing solution dispenser. The complimentary member is separable from the patient's tubing so that after the sterilization is effected, the complimentary member is separated from the patient's tubing and is removed from the pouch.

In another embodiment of the invention, the flexible housing comprises a pleated, substantially collapsible housing. In that embodiment, the housing includes a steam inlet for coupling to a steam generator and also includes a pressure regulating valve.

In a further form of the invention, the flexible housing comprises a tube. A first clamp is provided for clamping the first area of the tube around the transfer tube and a second clamp is provided for clamping the second area around the patient's tube. The tube is formed of a thermoplastic material and has a heat seal adjacent the second area to form a reservoir area.

In accordance with the invention, a sterile connection process for a continuous ambulatory peritoneal dialysis is provided. The process includes the steps of providing a flexible housing having one end thereof connected to the transfer port. The patient's tubing is attached to the opposite end of the flexible housing and a sterilizing agent is introduced into the housing and in contact with the transfer port and the patient's tubing. Thereafter, the sterilized transfer port and the sterilized patient's tubing are connected together within the housing.

A more detailed explanation of the invention is provided in the following description and claims, and is illustrated in the accompanying drawings.

BRIEF DESCRIPTION OF THE DRAWINGS

FIG. 1 is an elevational view of a portion of a sterile connection system constructed in accordance with principles of the present invention, showing the dialysis solution bag with a flexible housing connected thereto;

FIG. 2 is a cross sectional view of the housing of FIG. 1, taken along the plane of the line 2—2 of FIG. 1;

FIG. 3 is an elevational view, partially broken for clarity, of an adapter member and sterilizing fluid dispenser for use in connection with the housing of FIG. 1;

FIG. 4 is a left side view thereof;

FIG. 5 is an elevational view of the end of a patient's tube, showing a luer connector for connecting to the adapter member of FIGS. 3-4;

FIG. 6 is a side elevational view thereof;

FIG. 7 is a view showing the connection of the luer connector of FIG. 5 to the adapter member of FIGS. 3-4;

FIG. 8 is an elevational view, partially broken for clarity, showing the FIG. 5 connector fastened to the FIG. 3 adapter members;

FIG. 9 is a view showing the connection of the FIG. 8 adapter member and patient's tube to the housing;

FIG. 10 is an elevational view, partially broken for clarity, of a sterile connection system constructed in accordance with the principles of the present invention;

FIG. 21 is an elevational view, partially broken for clarity, of the sterile connection system according to the third form of the present invention; and FIG. 22 is a view similar to the view of FIG. 21 but showing a subsequent step in use of the system.

DETAILED DESCRIPTION OF THE ILLUSTRATIVE EMBODIMENT

Figure 13:
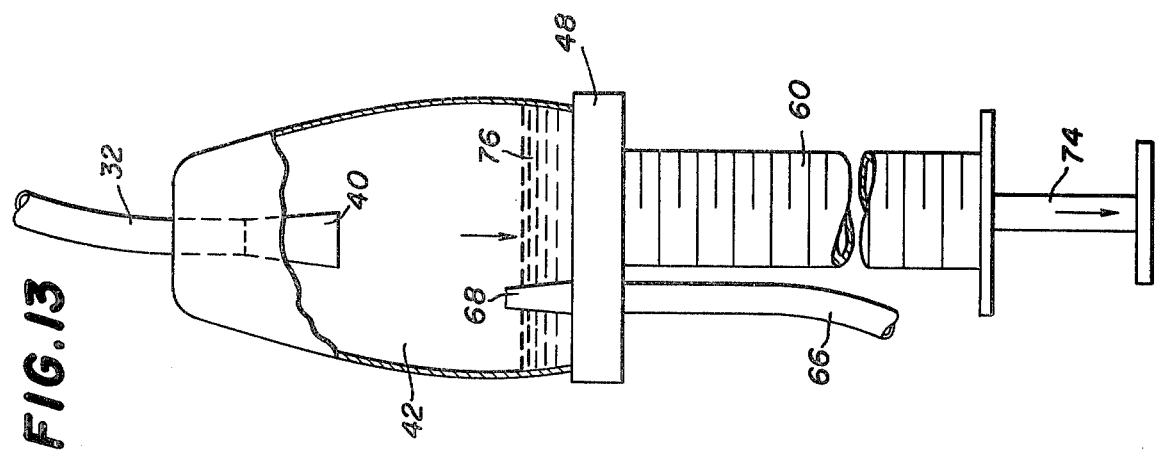
FIG. 13 is a view similar to the view of FIG. 12 but showing the withdrawal of the sterilizing fluid from the housing.

Referring to FIG. 1, a dialysis solution container 30 comprises a flexible foldable plastic bag having a transfer port 32 extending from one end thereof and also having an additional port 34 extending from the same end thereof with an injection site 36 connected to port 34. Transfer port 32 preferably includes a length of flexible plastic tubing 38 (see FIG. 10) having a connector 40 at its distal end. A flexible, transparent housing 42 is provided, having one end 44 thereof fastened to transfer port 32 by means of a pressure fit and/or solvent bonding. As can be seen most clearly in FIG. 2, connector 40 extends into the interior of flexible transparent housing 42.

The opposite end 46 of housing 42 has an adapter member 48 connected thereto for receiving a complimentary member 50 (FIG. 3). In the illustrative embodiment, adapter member 48 is ring-shaped and formed of plastic, and has an inwardly extending rim 52 for being received within the peripheral groove 54 of complimentary member 50. Complimentary member 50 defines an axial bore 56 which communicates with the chamber 58 of a syringe 60 which is fastened to the complimentary member 50. Syringe 60 contains a sterilizing fluid, such as Betadine, for introduction into housing 42 as explained below.

Complimentary member 50 defines a slot 62, the walls of which are adapted to receive a locking member 64 carried by plastic tube 66 which is coupled through one or more connectors to the patient's peritoneal cavity. As used herein, tubing such as tube 66 that is coupled to the patient's peritoneal cavity is sometimes referred to as the "patient's tube".

Locking member 64 is located adjacent to distal end of patient's tube 66 being formed by a connector 68. Connector 68 is adapted for coupling to connector 40 and connectors 68 and 40 may be male and female luer connectors. Blocking member 64 defines a grooved portion 70 which cooperates with flanged portion 72 (FIG. 3) to interlock patient's tube 66 with complimentary member 50.

As shown most clearly in FIGS. 7-9, patient's tube 66 is coupled to complimentary member 50 by sliding blocking member 64 into slot 62. The assembly which includes complimentary member 50, syringe 60 and patient's tube 66 is then inserted into adapter member 48 in the manner illustrated in FIG. 9. This serves to close end 46 of housing 42 so that the housing now becomes closed to the outside environment. The sterilization operation will now be described by referring to FIGS. 10-16.

Figure 12:
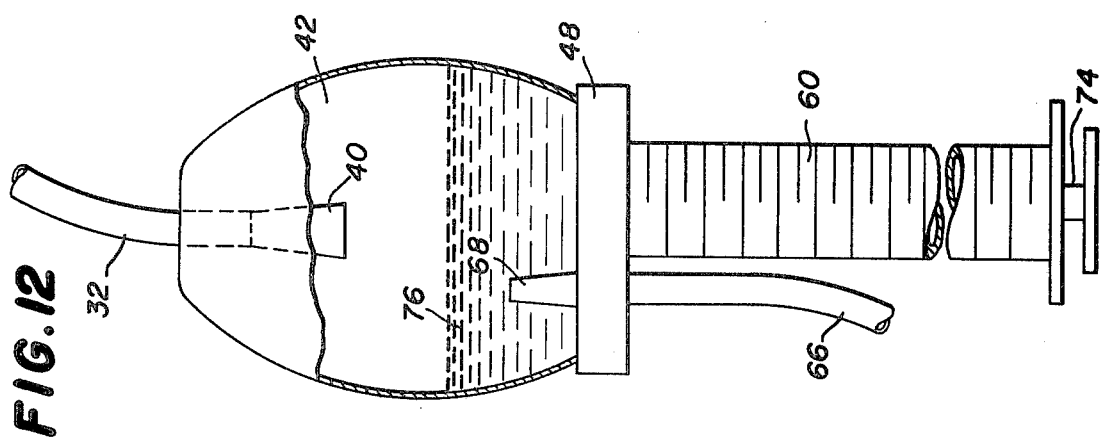
FIG. 12 is a view similar to the view of FIG. 11 but showing the sterilization of the patient's tube.
Figure 11:
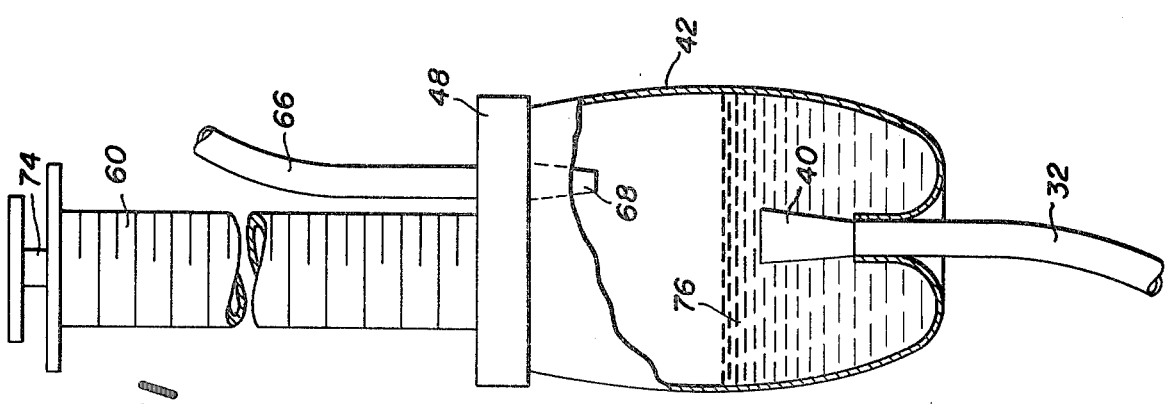
FIG. 11 is a view of the housing of FIG. 10, showing sterilization of the transfer port of the dialysis solution container.
Figure 14:
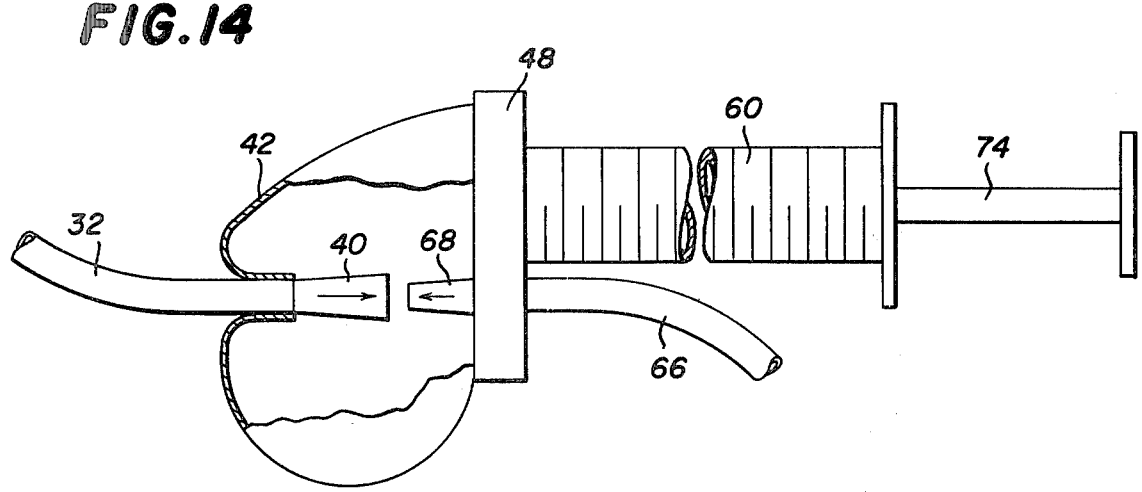
FIG. 14 is a view similar to FIG. 13 but showing the movement of the patient's tube toward the transfer port.
Figure 15:
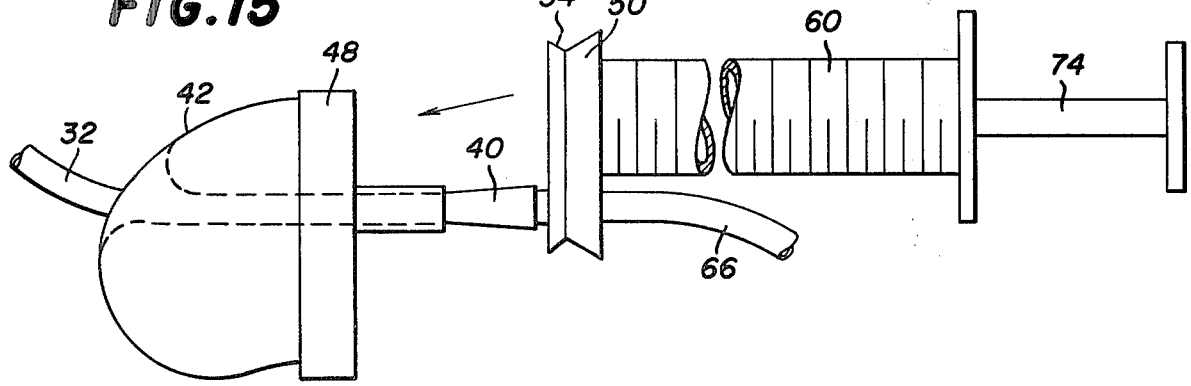
FIG. 15 is a view similar to the view of FIG. 14 but showing the coupling of the patient's tube to the transfer port.
Figure 16:
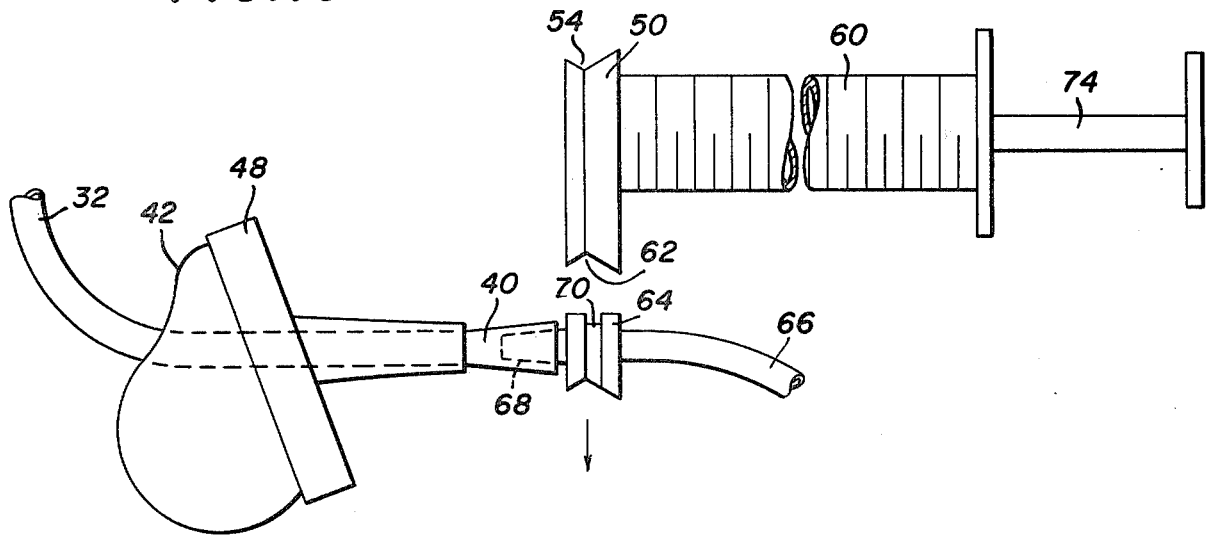
FIG. 16 is a view similar to FIG. 15 but showing the release of the adapter member from the patient's tube.

Syringe 60 is actuated by moving plunger 74 inwardly to force the sterilizing fluid 76 into housing 42. Referring to FIG. 11, syringe 60 is lifted upwardly so as to submerge connector 40 within sterilizing fluid 76. Referring to FIG. 12, the unit is then inverted to submerge connector 68 within sterilizing fluid 76. Referring to FIG. 13, plunger 74 is moved rearwardly to withdraw the sterilizing fluid from housing 42. Referring to FIG. 14, connectors 68 and 40 are then moved together so as to form the connection, adapter member 48 is withdrawn from complimentary member 50 (FIG. 15) and locking member 64 is released from slot 62 (FIG. 16). Connectors 40 and 68 have thus been sterilized and connected in the sterile environment.

Figure 17:
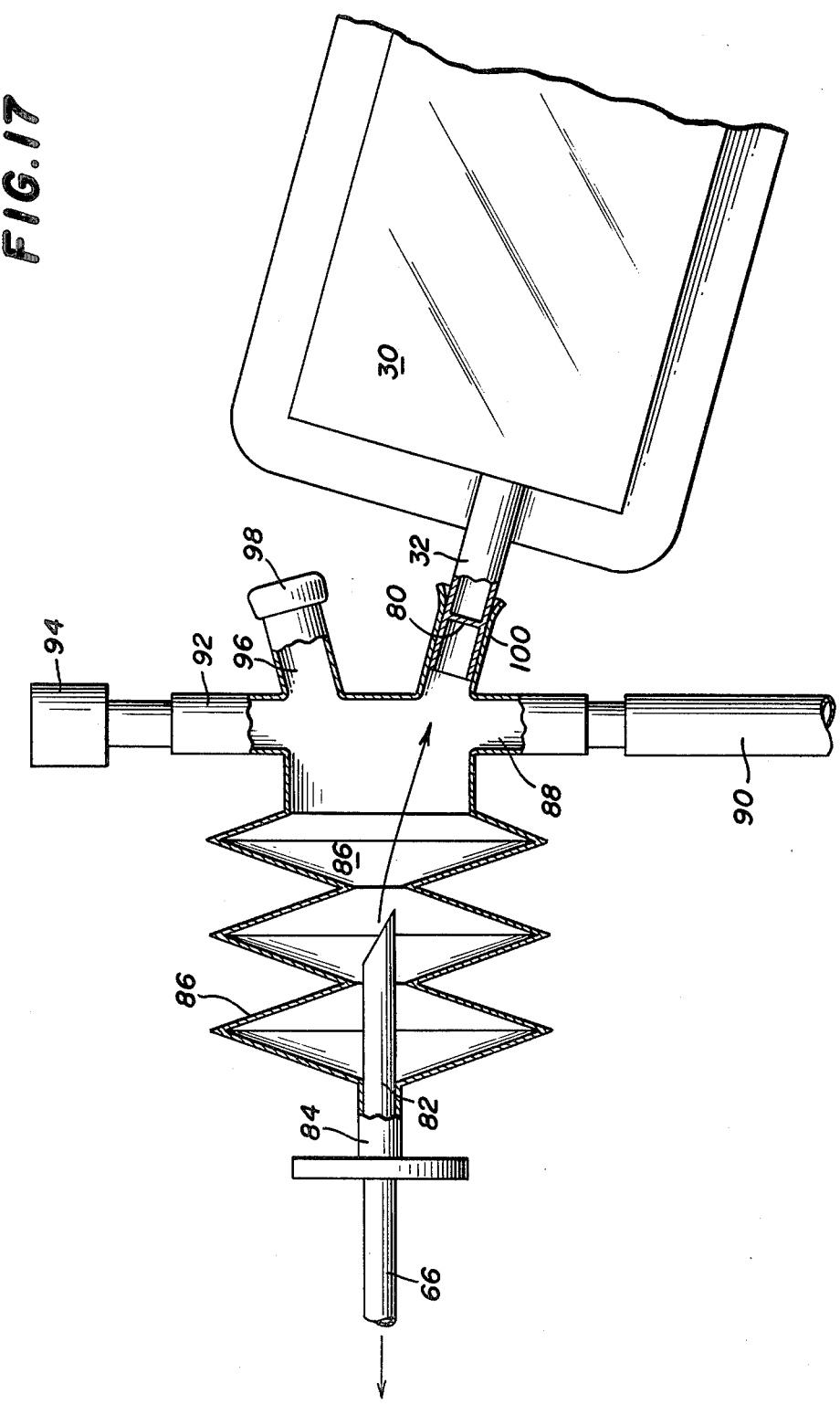
FIG. 17 is a sterile connection system constructed in accordance with the second embodiment of the present invention.

In the FIG. 17 embodiment, transfer port 32 of the dialysis solution bag 30 has a transverse membrane 80 which prevents fluid flow through the transfer port 32 until membrane 80 is broken. A spike connector 82 forms the distal end of the patient's tube 66, and spike connector 82 is inserted into tube port 84 at one end of a pleated, substantially collapsible housing 86. Pleated housing 86 is preferably formed of a plastic material in a bellows form and includes a port 88 for coupling to line 90 from a steam generator and a port 92 to which a pressure regulating valve 94 is connected for regulating the pressure in order to obtain the proper sterilizing temperature.

A pair of ports 96 (covered with cap 98) and 100 are provided for receiving the transfer ports 32 of dialysis solution bags 30. Thus the transfer port of a spent solution bag 30 may be coupled to port 100 while a fresh solution bag is coupled to port 96.

In the operation of the device, port 100 is securely fastened to transfer port 32 of a solution bag 30 by a pressure fit and/or solvent bonding and the spike connector 82 of the patient's tube 66 is inserted into port 84. A sterilizing fluid such as the steam via line 90 or any other suitable type of sterilizing fluid is then introduced into the housing 86. Once spike 82 and the distal end portions of transfer port 32 are sterilized, spike 82 is then moved by the patient toward transfer port 32 whereby the bellows forming housing 86 will substantially collapse allowing the spike to enter transfer port 32 and piece membrane 80. The sterile connection is now complete and tube 90 may be disconnected from the housing.

The dialysis solution from solution bag 30 may then be introduced into the patient's peritoneal cavity via tube 66, and the solution will remain within the patient's peritoneal cavity for a predetermined period of time, for example, four hours. After the predetermined period of time, the dialysis solution in the patient's peritoneal cavity is drained back into solution bag 30. A fresh solution bag may be coupled to port 96 by pressure fitting and/or solvent bonding the transfer port 32 of the fresh solution bag 30 to the port 96. Spike 82 is removed from transfer port 32 of the spent solution bag and a sterilizing agent, such as steam, is introduced into the housing 86. Once spike 82 and the distal end portions of transfer port 32 of the fresh solution bag 30 are sterilized, spike 82 is then moved by the patient toward port 96 and transfer port 32 of the fresh solution bag whereby the bellows forming housing 86 will substantially collapse allowing spike 82 to enter transfer port 32 of the fresh solution bag and to pierce membrane 80 of the fresh solution bag. Thus the spike 82 has been removed from the spent dialysis solution bag, has been sterilized and has been inserted into the transfer port of a fresh dialysis solution bag for subsequent processing.

Figure 18:
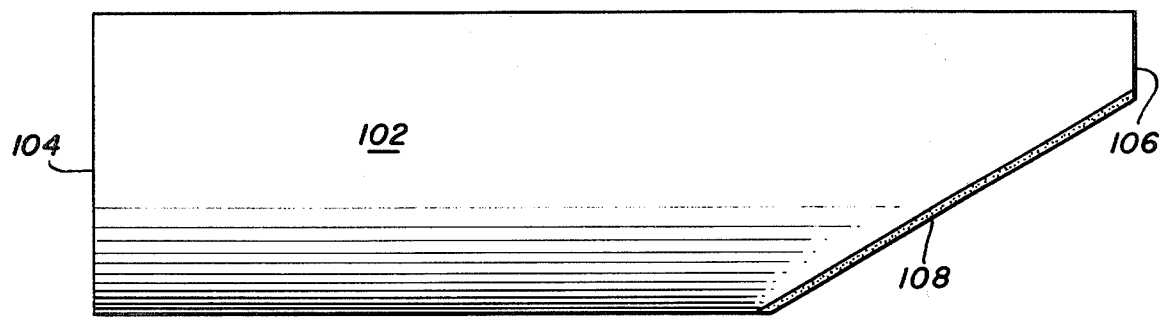
FIG. 18 is an elevational view of a flexible tube for use with a sterile connection system constructed in accordance with the third form of the present invention.

In the FIGS. 18–22 embodiment, a flexible plastic tube 102 is provided having a large open end 104 and a smaller open end 106 which is formed by heat sealing tube 102 along line 108, as illustrated in FIG. 18. Tube 106 is preferably formed of polyethlene or polyvinyl chloride and is transparent so that the patient can observe the connection of the patient's tube to the transfer tube.

Figure 19:
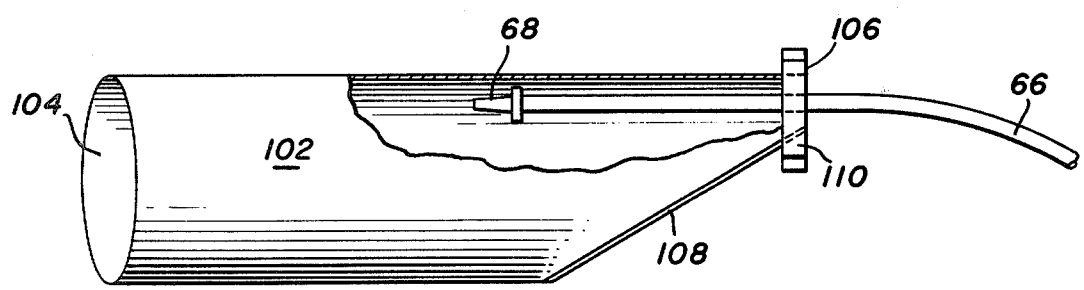
FIG. 19 is a view of the tube of FIG. 18, showing the coupling of the patient's thereto.

As illustrated in FIG. 19, the patient's tube 66 is inserted into end 106 and a clamp 110 is provided to close end 106 about patient's tube 66. A removable clamp 110 may be utilized or a permanent connection may be made by means of a heat seal at end 106 to seal end 106 to the patient's tube 66.

Figure 20:
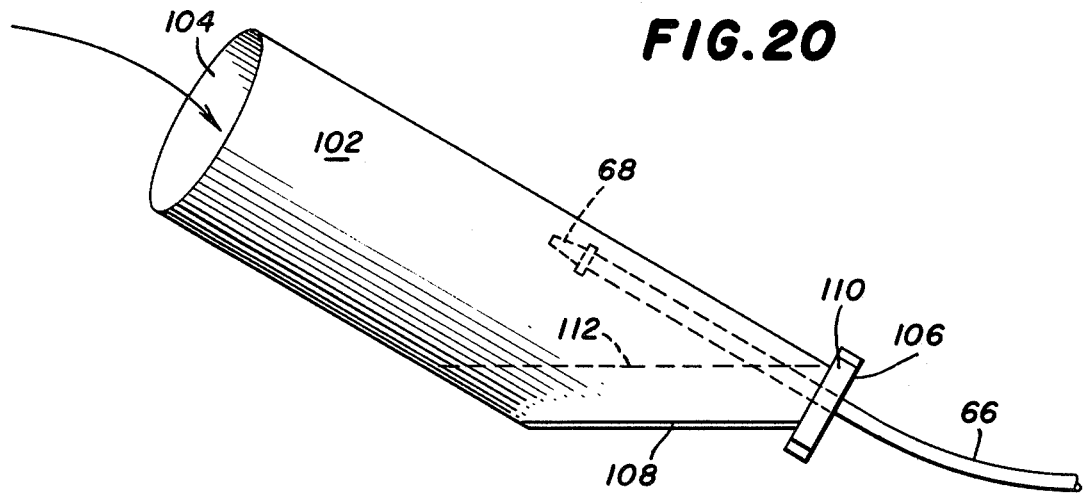
FIG. 20 is a view similar to the FIG. 19 view, showing the introduction of sterilization fluid into the housing.

The angled portion resulting from heat seal 108 is utilized as a reservoir. Thus, a sterilizing fluid such as Betadine is introduced into the tube through end 104 and the sterilizing fluid will be held in the reservoir created by the angled portion, as illustrated in FIG. 20.

Thereafter, the transfer port 32 is extended into housing 102 through end 104 and the clamp 114 is provided to seal end 104 about port 32. Housing 102 is flexible enough to allow the operator to manipulate the housing to remove cap 116 which covers the end of connector 40. Thereafter, the housing is moved appropriately so as to enable the sterilizing fluid 112 to contact the exposed surfaces of transfer port 32, connector 40, patient's tube 66 and connector 68. After the appropriate dwell time, the housing 102 is tilted so that sterilizing fluid 112 flows into the reservoir area and sterilized connectors 68 and 40 are coupled together to complete the sterile system. One of the clamps may be removed and the sterilizing fluid 112 is poured out, with the patient having the option to cut tube 102 with scissors and discard it, leaving coupled connectors 68 and 40 free of the tube 102.

The transfer port 32a of a fresh dialysis solution bag 30 may also be extended into housing 102 through end 104 with clamp 114 being provided to seal end 104 about ports 32 and 32a. In this manner, after the dialysis solution from the patient's peritoneal cavity has been drained back into the spent solution bag container by a transfer port 32, connector 68 is withdrawn from connector 40 and the housing is moved appropriately so as to enable the sterilizing fluid 112 to contact the exposed surfaces of transfer port 32a, connector 40a, patient's tube 66 and connector 68. After the appropriate dwell time, sterilized connectors 68 and 40a are coupled together and fresh dialysate solution is introduced through transfer port 32a to patient's tube 66 and to the patient's peritoneal cavity.

It is seen that the sterile connection system has been described in which flexible housing is utilized to provide an environment in which the patient's tube and the transfer port from a solution container are sterilized. It is to be understood, however, that the present system is applicable to other sterilization uses in which two or more tubes are to be sterilized and connected together. Although three illustrative embodiments of the invention have been shown and described, it is to be understood that various modifications and substitutions may be made by those skilled in the art without departing from the novel spirit and scope of the present invention.

What is claimed is:

1. A sterile connection system for continuous ambulatory peritoneal dialysis in which a dialysis solution container having a transfer port is coupled to tubing extending from a patient's peritoneal cavity, the improvement comprising:
   a flexible housing having a first area thereof for attachment to said transfer port and a second, spaced area thereof for attachment to said patient's tubing;
   said attachment areas defining openings for enabling the transfer port and patient's tubing to extend into the interior of said flexible housing when attached thereto;
   said flexible housing having means for receiving a sterilizing fluid therein and being operable to enable the transfer port and the patient's tubing to be sterilized within the housing and also connected to each other within the housing.

2. A sterile connection system as described in claim 1, said patient's tubing having a connector member at its distal end.

3. A sterile connection system as described in claim 1, said transfer port including a length of flexible tubing having a connector member at its distal end.

4. A sterile connection system as described in claim 1, including means fastening said flexible housing to said transfer port at said first area.

5. A sterile connection system as described in claim 4, said secondary area including a receptacle for enabling attachment of the patient's tubing thereto by the patient.

6. A sterile connection system as described in claim 1, said flexible housing comprising a flexible pouch with said first area at one end thereof and said second area at the opposite end thereof.

7. A sterile connection system as described in claim 6, including means fastening said transfer port to said first attachment area, and an adapter member for connection to said second area to couple the patient's tubing to said flexible pouch.

8. A sterile connection system as described in claim 7, said adapter member having means for receiving a complimentary member carrying said patient's tubing, with said complimentary member being operative to close said pouch.

9. A sterile connection system as described in claim 8, said complimentary member having means for receiving the patient's tubing and carrying a sterilizing fluid dispenser.

10. A sterile connection system as described in claim 9, said sterilizing fluid dispenser comprising a syringe.

11. A sterile connection system as described in claim 9, said complimentary member being separable from the patient's tubing whereby after the sterilization is effected, the complimentary member is separated from the patient's tubing and is removed from the pouch.

12. A sterile connection system for continuous ambulatory peritoneal dialysis in which a dialysis solution container having a transfer port is coupled to tubing extending from a patient's peritoneal cavity, the improvement comprising:
a flexible pouch having a first area at one end thereof for attachment to said transfer port and a second area at the opposite end thereof for attachment to said patient's tubing;
said patient's tubing having a connector member at its distal end;
said transfer port including a length of flexible tubing having a connector member at its distal end;
said attachment areas defining openings for enabling the transfer port and patient's tubing to extend into the interior of said flexible pouch when attached thereto;
means fastening said transfer port to said first attachement area, and an adapter member for connection to said second attachment area and to couple the patient's tubing to said flexible pouch;
said adapter member having means for receiving a complimentary member carrying said patient's tubing, with said complimentary member being operative to close said pouch, said complimentary member having means for receiving the patient's tubing and carrying a sterilizing fluid dispenser;
said flexible pouch having means for receiving a sterilizing fluid therein from said sterilizing fluid dispenser and being operable to enable the transfer port and the patient's tubing to be sterilized within the housing and also be connected to each other within the housing;
said complimentary member being separable from the patient's tubing whereby after the sterilization is effected the complimentary member is separated from the patient's tubing and is removed from the pouch.

13. A sterile connection system as described in claim 12, in which said sterilizing fluid dispenser comprises a syringe.

14. A sterile connection system as described in claim 1, said flexible housing comprising a pleated, substantially collapsible housing with said first area at one end thereof and said second area at the opposite end thereof.

15. A sterile connection system as described in claim 14, said first area comprising a tube port for pressure attachment for said transfer port.

16. A sterile connection system as described in claim 14, said second area comprising means for receiving a spike connector forming the distal end of the patient's tubing.

17. A sterile connection system as described in claim 14, said housing including a steam inlet for coupling to a steam generator, and a pressure relief valve.

18. A sterile connection system for continuous ambulatory peritoneal dialysis in which a dialysis solution container having a transfer port is coupled to tubing extending from a patient's peritoneal cavity, the improvement comprising:
a pleated, substantially collapsible housing having a first area at one end thereof for attachment to said transfer port and a second area at the opposite end thereof for attachment to said patient's tubing;
said attachment areas defining openings for enabling the transfer port and the patient's tubing to extend into the interior of said housing when attached thereto;
said first area comprising a tube port for pressure attachment to said transfer port and said second area comprising means for receiving a spike connector forming the distal end of the patient's tubing;
said housing having means for receiving a sterilizing fluid therein and being operable to enable the transfer port and the patient's tubing to be sterilized within the housing and also connected to each other within the housing.

19. A sterile connection system as described in claim 18, said housing including a steam inlet for coupling to a steam generator, and a pressure regulating valve.

20. A sterile connection system as described in claim 1, said flexible housing comprising a tube with said first area at one end thereof and said second area at the opposite end thereof.

21. A sterile connection system as described in claim 20, including a first clamp for clamping said first area around said transfer tube and a second clamp for clamping said second area around the patient's tube.

22. A sterile connection system as described in claim 20, said tubing formed of a thermoplastic material and having a heat seal adjacent said second area to form a reservoir area.

23. A sterile connection system for enabling the sterile connection of a first tube to a second tube, which comprises:
a flexible housing having a first area thereof for attachment to one of said tubes and a second, spaced area thereof for attachment to the other of said tubes;
said attachment areas defining openings for enabling the tubes to extend into the interior of said flexible housing when attached thereto;
said flexible housing having means for receiving a sterilizing fluid therein and being operable to enable the tubes to be sterilized within the housing and also connected to each other within the housing.

24. A sterile connection process for continuous ambulatory peritoneal dialysis in which a dialysis solution container having a transfer port is coupled to tubing extending from a patient's peritoneal cavity, the improvement comprising the steps of:
providing a flexible housing having one end thereof connected to the transfer port;
attaching the patient's tubing to the opposite end of the flexible housing;
introducing a sterilizing fluid into the housing and in contact with the transfer port and patient's tubing; and
connecting within the housing the sterilized transfer port to the sterilized patient's tubing.

25. A sterile connection process for continuous ambulatory peritoneal dialysis in which a dialysis solution container having a transfer port is coupled to tubing extending from a patient's peritoneal cavity, the improvement comprising the steps of:
providing a flexible housing having one end thereof connected to the transfer port of a first dialysis solution container;
attaching the patient's tubing to the opposite end of the flexible housing;
introducing a sterilizing fluid into the housing and in contact with the transfer port and patient's tubing;
connecting within the housing the sterilized transfer port to the sterilized patient's tubing;
introducing the dialysis solution from the first dialysis solution container via the patient's tubing to the patient's peritoneal cavity;
thereafter draining the solution from the patient's peritoneal cavity back into the first dialysis solution container;
connecting the transfer port of a second dialysis solution container to said one end of the flexible housing;
removing the patient's tubing from the transfer port to the first dialysis solution container;
introducing a sterilizing fluid into the housing and in contact with the transfer port of the second dialysis solution container and the patient's tubing; and
connecting within the housing the sterilized transfer port of the second dialysis solution container to the sterilized patient's tubing.

26. A sterile connection process for continuous ambulatory peritoneal dialysis in which a dialysis solution container having a transfer port is coupled to tubing extending from a patient's peritoneal cavity, the improvement comprising the steps of:
providing a flexible housing;
attaching the transfer port to one end of the flexible housing;
attaching the patient's tubing to the other end of the flexible housing to thereby close the housing;
introducing a sterilizing fluid into the housing;
contacting the transfer port and the patient's tubing with the sterilizing fluid; and
thereafter connecting within the closed housing the sterilized transfer port to the sterilized patient's tubing.

27. A sterile connection system for enabling the sterile connection of a first tube to a second tube, which comprises:
a flexible pouch having a first area at one end thereof for attachment to one of said tubes and a second area at the opposite end thereof for attachment to the other of said tubes;
said attachment areas defining openings for enabling the tubes to extend into the interior of said flexible pouch when attached thereto;
means fastening said first tube to said first attachment area, and an adapter member for connection to said second attachment area and to couple the second tube to said flexible pouch;
said adapter member having means for receiving a complimentary member carrying said second tube, with said complimentary member being operative to close said pouch, said complimentary member having means for receiving said second tube and carrying a sterilizing fluid dispenser;
said flexible pouch having means for receiving a sterilizing fluid therein from said sterilizing fluid dispenser and being operable to enable said first tube and said second tube to be sterilized within the housing and also be connected to each other within the housing;
said complimentary member being separable from said second tube whereby after the sterilization is effected the complimentary member is separated from the second tube and is removed from the pouch.

28. A sterile connection system for enabling the sterile connection of a first tube to a second tube, which comprises:
a pleated, substantially collapsible housing having a first area at one end thereof for attachment to said first tube and a second area at the opposite end thereof for attachment to said second tube;
said attachment areas defining openings for enabling the tubes to extend into the interior of said housing when attached thereto;
said first area comprising a tube port for pressure attachment to said first tube and said second area comprising means for receiving a spike connector forming the distal end of the second tube;
said housing having means for receiving a sterilizing fluid therein and being operable to enable the tubes to be sterilized within the housing and also connected to each other within the housing.

* * * * *